US006544790B1

(12) United States Patent
Sabatini

(10) Patent No.: US 6,544,790 B1
(45) Date of Patent: Apr. 8, 2003

(54) REVERSE TRANSFECTION METHOD

(75) Inventor: David M. Sabatini, Cambridge, MA (US)

(73) Assignee: Whitehead Institute for Biomedical Research, Cambridge, MA (US)

(*) Notice: Subject to any disclaimer, the term of this patent is extended or adjusted under 35 U.S.C. 154(b) by 0 days.

(21) Appl. No.: 09/664,297

(22) Filed: Sep. 18, 2000

Related U.S. Application Data

(60) Provisional application No. 60/193,580, filed on Mar. 30, 2000, and provisional application No. 60/154,737, filed on Sep. 17, 1999.

(51) Int. Cl.[7] .................. C12N 15/63; C12N 15/85; C12N 15/87; C12N 15/00; C12N 15/09
(52) U.S. Cl. .................. 435/455; 435/320.1; 435/440; 435/6; 435/7.21; 435/174
(58) Field of Search .................. 435/6, 440, 320.1, 435/7.21, 455, 174; 422/50

(56) References Cited

U.S. PATENT DOCUMENTS

| | | | |
|---|---|---|---|
| 4,591,567 A | | 5/1986 | Britten et al. |
| 5,445,934 A | | 8/1995 | Fodor et al. |
| 5,654,185 A | | 8/1997 | Palsson |
| 5,744,305 A | | 4/1998 | Fodor et al. |
| 5,804,431 A | * | 9/1998 | Palsson et al. ........... 435/235.1 |
| 5,807,522 A | * | 9/1998 | Brown et al. ................. 422/50 |
| 5,811,274 A | | 9/1998 | Palsson |
| 5,851,818 A | | 12/1998 | Huang et al. |
| 6,025,337 A | | 2/2000 | Truong et al. |
| 6,110,426 A | | 8/2000 | Shalon et al. |
| 6,133,026 A | | 10/2000 | Huang et al. |

FOREIGN PATENT DOCUMENTS

| | | |
|---|---|---|
| WO | WO 95 35505 | 12/1995 |
| WO | WO 96 17948 | 7/1996 |
| WO | WO 99 55886 | 11/1999 |
| WO | WO 99/57311 | 11/1999 |
| WO | WO 99/57312 | 11/1999 |
| WO | WO 00/63407 | 10/2000 |

OTHER PUBLICATIONS

Leong et al., DNA–polycation nanospheres as non-viral gene delivery vehicles, 1998, Journal of Controlled Release, vol. 53, pp. 183–193.*
Simonsen, H. and Lodish, H.F., "Cloning By Function: Expression Cloning in Mammalian Cells," *TiPS*, 15:437–441 (Dec. 1994).
Strausberg, R.L., et al., "The Mammalian Gene Collection," *Science*, 286(5439):455–457 (Oct. 15, 1999).
Schena, M., "Genome Analysis With Gene Expression Microarrays," *BioEssays*, 18(5):427–431 (May 1996).
Schena, M., et al., "Parallel Human Genome Analysis: Microarray–based Expression Monitoring of 1000 Genes," *Proc. Natl. Acad. Sci. USA*, 93(20):10614–10619 (Oct. 1996).
Schena, M., et al., "Microarrays: Biotechnology's Discovery Platform for Functional Genomics," *TIBTech*, 16:301–306 (Jul. 1998).

Anchordoquy, T.J. et al., "Maintenance of transfection rates and physical characterization of lipid/DNA complexes after freeze–drying and rehydration," Arch. Biochem. Biophys. 348:199–206 (1997).
Anchordoquy, T.J. et al., "Stability of lipid/DNA complexes during agitation and freeze–thawing," J. Pharm. Sci. 87:1046–51 (1998).
Bielinska, A.U. et al., "DNA complexing with polyamidoamine dendrimers: Implications for transfection," Bioconjug. Chem. 10:843–50 (1999).
Chenrg, J.Y. et al., "Freeze–drying of poly((2–dimethylamino)ethyl methacrylate)–based gene delivery systems," Pharm. Res. 14:1838–41 (1997).
Eastman, S.J. et al., "Biophysical characterization of cationic lipid: DNA complexes," Biochim. Biophys. Acta 1325:41–62 (1997).
Hong, K. et al., "Stabilization of cationic liposome–plasmid DNA complexes by polyamines and poly(thylene glycol-)–phospholipid conjugates for efficient in vivo gene delivery," FEBS. Lett. 400:233–37 (1997).
Leong, K.W. et al., "DNA–polycation nanospheres as non-viral gene delivery vehicles," Journal of Controlled Release 53:183–193 (1998).
Lueking, A. et al., "Protein microarrays for gene expression and antibody screening," Anal. Biochem. 270:103–11 (1999).
MacBeath, G. et al., "Printing proteins as microarrays for high–throughput function determination," Science 289:1760–63 (2000).
Pires, P. et al., "Interaction of cationic liposomes and their DNA complexes with monocytic leukemia cells," Biochim. Biophys. Acta 1418:71–84 (1999).
Russell, D.W. et al., "Human gene targeting by viral vectors," Nat. Genet. 18:325–30 (1998).
Stegmann, T. et al., "Gene Transfer Mediated by Cationic Lipids: Lack of a Correlation Between Lipid Mixing and Transfection," Biochim. Biophys. Acta 1325:71–9 (1997).
Talsma, H. et al.,"Stabilization of gene delivery systems by freeze–drying," Int. J. Pharm. 157:233–238 (1997).
Uyttersprot, N. et al., "A new tool for efficient transfection of dog and human thyrocytes in primary culture," Mol. Cell. Endocrinol. 142:35–9 (1998).
Whitney, M. et al., "A genome–wide functional assay of signal transduction in living mammalian cells," Nat. Biotechnol. 163:1329–33 (1998).
Zanta, M.A. et al., "Gene delivery: A single nuclear localization signal peptide is sufficient to carry DNA to the cell nucleus," Proc. Natl. Acad. Sci. U.S.A. 96:91–6 (1999).
Zhu, H. et al., "Analysis of yeast protein kinases using protein chips," Nat. Genet. 26:283–89 (2000).
Ziauddin, J. et al., "Microarrays of cells expressing defined cDNAs," Nature 411:107–110 (2001).

* cited by examiner

Primary Examiner—Remy Yucel
Assistant Examiner—Konstantina Katcheves
(74) Attorney, Agent, or Firm—Clark & Elbing LLP; Kristina Bieker-Brady

(57) ABSTRACT

A reverse transfection method of introducing DNA of interest into cells and arrays, including microarrays, of reverse transfected cells.

151 Claims, 6 Drawing Sheets

HEK293T cells reverse transfected with HA-GST and detected via anti-HA immunofluorescence HEK293T cells reverse transfected with pBABE EGFP FIG. 4D
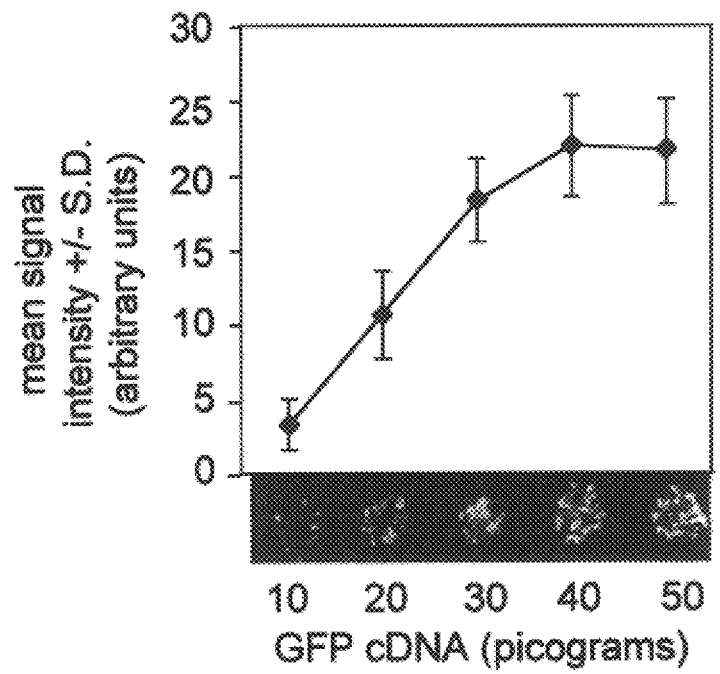
FIG. 4E
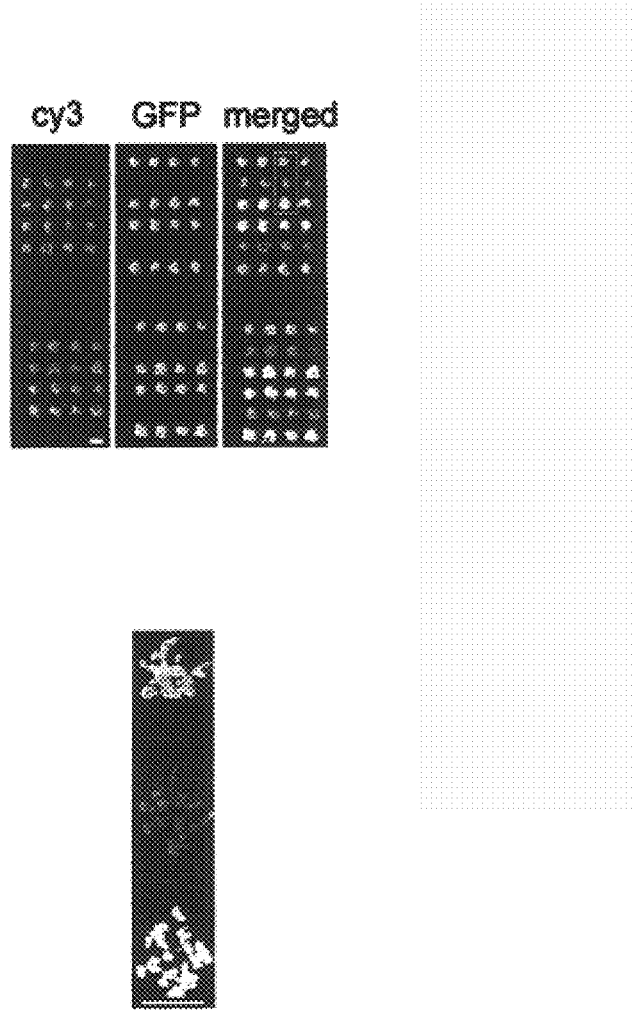
FIG. 4F

US 6,544,790 B1

REVERSE TRANSFECTION METHOD

RELATED APPLICATIONS

This application claims the benefit of U.S. application Ser. No. 60/193,580, filed Mar. 30, 2000 and U.S. application Ser. No. 60/154,737, filed Sep. 17, 1999. The entire teachings of U.S. application Ser. No. 60/193,580 and U.S. application Ser. No. 60/154,737 are incorporated herein by reference.

BACKGROUND OF THE INVENTION

Genome and expressed sequence tag (EST) projects are rapidly cataloging and cloning the genes of higher organisms, including humans. The emerging challenge is to uncover the functional roles of the genes and to quickly identify gene products with desired properties. The growing collection of gene sequences and cloned cDNAs demands the development of systematic and high-throughput approaches to characterizing the gene products. The uses of DNA microarrays for transcriptional profiling and of yeast two-hybrid arrays for determining protein-protein interactions are recent examples of genomic approaches to the characterization of gene products (Schena, M., et al., *Nature*, 10:623 (2000)). Comparable strategies do not exist to analyze the function, within mammalian cells, of large sets of genes. Currently, in vivo gene analysis can be done—on a gene-by-gene scale—by transfecting cells with a DNA construct that directs the overexpression of the gene product or inhibits its expression or function. The effects on cellular physiology of altering the level of a gene product is then detected using a variety of functional assays.

A variety of DNA transfection methods, such as calcium phosphate coprecipitation, electroporation and cationic liposome-mediated transfection (e.g., lipofection) can be used to introduce DNA into cells and are useful in studying gene regulation and function. Additional methods, particularly high throughput assays that can be used to screen large sets of DNAs to identify those encoding products with properties of interest, would be useful to have available.

SUMMARY OF THE INVENTION

Described herein is a strategy for the high throughput analysis of gene function in mammalian cells. A method to create transfected cell microarrays that are suitable for rapidly screening large sets of cDNAs or DNA constructs for those encoding desired products or for causing cellular phenotypes of interest is described. Using a slide printed with sets of cDNAs in expression vectors, a living microarray of cell clusters expressing the gene products has been generated. The cell clusters can be screened for any property detectable on a surface and the identity of the responsible cDNA(s) determined form the coordinates of the cell cluster with a phenotype of interest.

Accordingly, the present invention relates to a method, referred to as a reverse transfection method, in which a defined nucleic acid (a nucleic acid of known sequence or source), also referred to as a nucleic acid of interest or a nucleic acid to be introduced into cells, is introduced into cells in defined areas of a lawn of eukaryotic cells, in which it will be expressed or will itself have an effect on or interact with a cellular component or function. Any suitable nucleic acid such as an oligonucleotide, DNA and RNA can be used in the methods of the present invention. The particular embodiments of the invention are described in terms of DNA. However, it is to be understood that any suitable nucleic acid is encompassed by the present invention.

In one embodiment, the present invention relates to a method in which defined DNA (DNA of known sequence or source), also referred to as DNA of interest or DNA to be introduced into cells, is introduced into cells in defined areas of a lawn of eukaryotic cells, in which it will be expressed or will itself have an effect on or interact with a cellular component or function. In the method, a mixture, defined below, comprising DNA of interest (such as cDNA or genomic DNA incorporated in an expression vector) and a carrier protein is deposited (e.g., spotted or placed in small defined areas) onto a surface (e.g., a slide or other flat surface, such as the bottoms of wells in a multi-welled plate) in defined, discrete (distinct) locations and allowed to dry, with the result that the DNA-containing mixture is affixed to the surface in defined discrete locations.

Such locations are referred to herein, for convenience, as defined locations. The DNA-containing mixture can be deposited in as many discrete locations as desired. The resulting product is a surface bearing the DNA-containing mixture in defined discrete locations; the identity of the DNA present in each of the discrete locations (spots) is known/defined. Eukaryotic cells, such as mammalian cells (e.g., human, monkey, canine, feline, bovine, or murine cells), bacterial, insect or plant cells, are plated (placed) onto the surface bearing the DNA-containing mixture in sufficient density and under appropriate conditions for introduction/ entry of the DNA into the eukaryotic cells and expression of the DNA or its interaction with cellular components. Preferably, the eukaryotic cells (in an appropriate medium) are plated on top of the dried DNA-containing spots at high density (e.g., $1 \times 10^5/cm^2$), in order to increase the likelihood that reverse transfection will occur. The DNA present in the DNA-containing mixture affixed to the surface enters eukaryotic cells (reverse transfection occurs) and is expressed in the resulting reverse transfected eukaryotic cells.

In one embodiment of the method, referred to as a "gelatin-DNA" embodiment, the DNA-containing mixture, referred to herein as a gelatin-DNA mixture, comprises DNA (e.g., DNA in an expression vector) and gelatin, which is present in an appropriate solvent, such as water or double deionized water. The mixture is spotted onto a surface, such as a slide, thus producing a surface bearing (having affixed thereto) the gelatin-DNA mixture in defined locations. The resulting product is allowed to dry sufficiently that the spotted gelatin-DNA mixture is affixed to the slide and the spots remain in the locations to which they have become affixed, under the conditions used for subsequent steps in the method. For example, a mixture of DNA in an expression vector and gelatin is spotted onto a slide, such as a glass slide coated with Σ poly-L-lysine (e.g., Sigma, Inc.), for example, by hand or using a microarrayer. The DNA spots can be affixed to the slide by, for example, subjecting the resulting product to drying at room temperature, at elevated temperatures or in a vacuum-dessicator. The length of time necessary for sufficient drying to occur depends on several factors, such as the quantity of mixture placed on the surface and the temperature and humidity conditions used.

The concentration of DNA present in the mixture will be determined empirically for each use, but will generally be in the range of from about 0.01 µg/µl to about 0.2 µg/µl and, in specific embodiments, is from about 0.02 µg/µl to about 0.10 µg/µl. Alternatively, the concentration of DNA present in the mixture can be from about 0.01 µg/µl to about 0.5 µg/µl, from about 0.01 µg/µl to about 0.4 µg/µl and from about 0.01 µg/µl to about 0.3 µg/µl. Similarly, the concentration of gelatin, or another carrier macromolecule, can be determined empirically for each use, but will generally be in the range of 0.01% to 0.5% and, in specific embodiments, is from about 0.05% to about 0.5%, from about 0.05% to about 0.2% or from about 0.1% to about 0.2%. The final concentration of DNA in the mixture (e.g., DNA in gelatin) will generally be from about 0.02 µg/µl to about 0.1 µg/µl and in a specific embodiment described herein, DNA is diluted in 0.2% gelatin (gelatin in water) to produce a final concentration of DNA equal to approximately 0.05 µg/µl.

If the DNA used is present in a vector, the vector can be of any type, such as a plasmid or viral-based vector, into which DNA of interest (DNA to be expressed in reverse transfected cells) can be introduced and expressed (after reverse transfection) in recipient cells. For example, a CMV-driven expression vector can be used. Commercially available plasmid-based vectors, such as pEGFP (Clontech) or pcDNA3 (Invitrogen), or viral-based vectors can be used. In this embodiment, after drying of the spots containing the gelatin-DNA mixture, the surface bearing the spots is covered with an appropriate amount of a lipid-based transfection reagent and the resulting product is maintained (incubated) under conditions appropriate for complex formation between the DNA in the spots (in the gelatin-DNA mixture) and the lipid-based transfection reagent. In one embodiment, the resulting product is incubated for approximately 20 minutes at 25° C. Subsequently, transfection reagent is removed, producing a surface bearing DNA (DNA in complex with transfection reagent), and cells in an appropriate medium are plated onto the surface. The resulting product (a surface bearing DNA and plated cells) is maintained under conditions that result in entry of the DNA into plated cells.

A second embodiment of the method is referred to as a "lipid -DNA" embodiment. In this embodiment, a DNA-containing mixture (referred to herein as a lipid-DNA mixture) which comprises DNA (e.g., DNA in an expression vector); a carrier protein (e.g., gelatin); a sugar, such as sucrose; a buffer that facilitates DNA condensation and an appropriate lipid-based transfection reagent is spotted onto a surface, such as a slide, thus producing a surface bearing the lipid-DNA mixture in defined locations. The resulting product is allowed to dry sufficiently that the spotted lipid-DNA mixture is affixed to the slide and the spots remain in the locations to which they have become affixed, under the conditions used for subsequent steps in the method. For example, a lipid-DNA mixture is spotted onto a slide, such as a glass slide coated with Σ poly-L-lysine (e.g., Sigma, Inc.), for example, by hand or using a microarrayer. The DNA spots can be affixed to the slide as described above for the gelatin-DNA method.

The concentration of DNA present in the mixture will be determined empirically for each use, but will generally be in the range of 0.5 µg/µl to 1.0 µg/µl. A range of sucrose concentrations can be present in the mixture, such as from about 0.1M to about 0.4M. Similarly, a range of gelatin concentrations can be present in the mixture, such as from about 0.01% to about 0.05%. In this embodiment, the final concentration of DNA in the mixture will vary and can be determined empirically. In specific embodiments, final DNA concentrations range from about 0.1 µg/µl to about 2.0 µg/µl. If a vector is used in this embodiment, it can be any vector, such as a plasmid, or viral-based vector, into which DNA of interest (DNA to be expressed in reverse transfected cells) can be introduced and expressed (after reverse transfection), such as those described for use in the gelatin-DNA embodiment.

After drying is complete (has occurred to a sufficient extent that the DNA remains affixed to the surface under the conditions used in the subsequent steps of the method), eukaryotic cells into which the DNA is to be reverse transfected are placed on top of the surfaces onto which the DNA-containing mixture has been affixed. Actively growing cells are generally used and are plated, preferably at high density (such as $1 \times 10^5/cm^2$), on top of the surface containing the affixed DNA-containing mixture in an appropriate medium, such as Dulbecco's Modified Eagles Medium (DMEM) containing 10% heat-inactivated fetal serum (IFS) with L-glutamine and penicillin/streptomycin (pen/strep). Other media can be used and their components can be determined based on the type of cells to be transfected. The resulting slides, which contain the dried lipid-DNA mixture and cells into which the DNA is to be reverse transfected, are maintained under conditions appropriate for growth of the cells and entry of DNA, such as an entry of an expression vector containing the DNA, into cells. In the present method, approximately one to two cell cycles are sufficient for reverse transfection to occur, but this will vary with the cell type and conditions used and the appropriate length of time for a specific combination can be determined empirically. After sufficient time has elapsed, slides are assessed for reverse transfection (entry of DNA into cells) and expression of the encoded product or effect of the introduced DNA on reverse-transfected cells, using known methods. This can be done, for example, by detecting immunofluorescence or enzyme immunocytochemistry, autoradiography, in situ hybridization or other means of detecting expression of the DNA or an effect of the encoded product or of the DNA itself on the cells into which it is introduced. If immunofluorescence is used to detect expression of an encoded protein, an antibody that binds the protein and is fluorescently labeled is used (e.g., added to the slide under conditions suitable for binding of the antibody to the protein) and the location (spot or area of the surface) containing the protein is identified by detecting fluorescence. The presence of fluorescence indicates that reverse transfection has occurred and the encoded protein has been expressed in the defined location(s) which show fluorescence. The presence of a signal, detected by the method used, on the slides indicates that reverse transfection of the DNA into cells and expression of the encoded product or an effect of the DNA in recipient cells has occurred in the defined location(s) at which the signal is detected. As described above, the identity of the DNA present at each of the defined locations is known; thus, when expression occurs, the identity of the expressed protein is also known.

Thus, the present invention relates, in one embodiment, to a method of expressing defined DNA, such as cDNA or genomic DNA, in defined locations or areas of a surface onto which different DNAs, such as DNA in a vector, such as an expression vector, has been affixed, as described herein. Because each area of the surface has been covered/spotted with DNA of known composition, it is a simple matter to identify the expressed protein. In addition, the present method is useful to identify DNAs whose expression alters (enhances or inhibits) a pathway, such as a signaling pathway in a cell or another property of a cell, such as its morphology or pattern of gene expression. The method is particularly useful, for example, as a high-throughput screening method, such as in a microarray format. It can be used in this format for identifying DNAs whose expression changes the phosphorylation state or subcellular location of a protein of interest or the capacity of the cell to bind a reagent, such as a drug or hormone ligand. In a second embodiment, which is also useful as a high-throughput screening method, DNA reverse transfected into cells has an effect on cells or interacts with a cellular component(s)

without being expressed, such as through hybridization to cellular nucleic acids or through antisense activity.

Also the subject of this invention are arrays, including microarrays, of defined DNAs spotted onto (affixed to) a surface and array: including microarrays of reverse transfected cells spotted to (affixed to) a surface by the method described herein. Such arrays can be produced by the gelatin-DNA embodiment or the lipid-DNA embodiment of the present method. Arrays of this invention are surfaces, such as slides (e.g., glass or Σ poly-L-lysine coated slides) or wells, having affixed thereto (bearing) in discrete, defined locations DNAs, such as cDNAs or genomic DNA, or cells containing DNA of interest introduced into the cells by the reverse transfection method described herein.

A method of making arrays of the present invention is also the subject of this invention. The method comprises affixing DNAs or reverse transfected cells onto a surface by the steps described herein for the gelatin-DNA embodiment or the lipid-DNA embodiment.

A DNA array of the present invention comprises a surface having affixed thereto, in discrete, defined locations, DNA of known sequence or source by a method described herein. In one embodiment, DNA is affixed to a surface, such as a slide, to produce an array (e.g., a macro-array or a micro-array) by spotting a gelatin-DNA mixture, as described herein, onto the surface in distinct, defined locations (e.g., by hand or by using an arrayer, such as a micro-arrayer) and allowing the resulting surface bearing the gelatin-DNA mixture to dry sufficiently that the spots remain affixed to the surface under conditions in which the arrays are used. In an alternative embodiment, DNA is affixed to a surface, such as a slide, to produce an array by spotting a lipid-DNA mixture, as described herein, onto the surface in distinct defined locations (e.g., by hand or by using an arrayer, such as a micro-arrayer) and allowing the resulting surface bearing the lipid-DNA mixture to dry sufficiently that the spots remain affixed to the surface under the conditions in which the arrays are used. This result in production of a surface bearing (having affixed thereto) DNA-containing spots.

An array of reverse transfected cells can also be produced by either embodiment described herein. In the gelatin-DNA embodiment, the steps described above for producing DNA arrays are carried out and subsequently, the surface bearing the DNA-containing spots is covered with an appropriate amount of a lipid-based transfection reagent and the resulting product is maintained (incubated) under conditions appropriate for complex formation between DNA in the spots and the reagent. After sufficient time (e.g., about 20 minutes at 25° C.) for complex formation to occur, transfection reagent is removed, producing a surface bearing DNA and cells in an appropriate medium are added. The resulting product (a surface bearing DNA and plated cells) is maintained under conditions that result in entry of DNA into plated cells, thus producing an array (a surface bearing an array) of reverse transfected cells that contain defined DNA and are in discrete, defined locations on the array. Such cell arrays are the subject of this invention.

In the lipid-DNA embodiment, the steps described above for producing DNA arrays are carried out and subsequently (after drying is sufficient to affix the DNA-containing spots to the surface, such as a slide or well bottom), cells are plated on top of the surface bearing the DNA-containing spots and the resulting slides, which contain the dried lipid-DNA mixture and cells to be reverse transfected, are maintained under conditions appropriate for growth of the cells and entry of DNA into the cells, thus producing an array (a surface bearing an array) of reverse transfected cells that contain defined DNA and are in discrete, defined locations on the array. Such arrays are the subject of this invention.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 4D is a graph of GFP cDNA (picograms) versus mean signal intensity +/− S.D. showing expression levels of clusters in a transfected cell microarray are proportional, over a four-fold range, to the amount of plasmid DNA printed on the slide. Arrays were printed with elements containing the indicated amounts of the GFP construct. Amount of DNA assumes a one nanoliter printing volume. After transfection, the mean +/− S.D. of the fluorescence intensities of the cell clusters were determined. Arrays were prepared as described in Example 3 except that the concentration of the GFP expression plasmid was varied from 0.010–0.050 $\mu$g/$\mu$l while the total DNA concentration was kept constant at 0.050 $\mu$g/$\mu$l with empty vector (prk5). Cell clusters were photographed and the signal intensity quantitated with Image Quant (Fuji). The fluorescent image is from a representative experiment.

FIG. 4E is a scan image showing that by printing mixtures of two plasmids, cotransfection is possible with transfected cell microarrays. Arrays with elements containing expression constructs for HA-GST, GFP or both were transfected and processed for anti-myc immunofluorescence. For immunofluorescence staining the cells were fixed as described in Example 3, permeabilized in 0.1% Triton X-100 in PBS for 15 minutes at room temperature and probed with primary and secondary antibodies as described. Primary antibodies were used for 1 hour at room temperature at the following concentrations: 1:500 anti-HA ascites (BaBCo), 2 µg/ml anti-myc 9E-10 (Calbiochem), 2 µg/ml anti-V5 (Invitrogen), or 10 µg/ml 4G10 anti-phosphotyrosine (Upstate Biotechnologies). The secondary antibody used was Cy3 µg/ml labeled anti-mouse antibody (Jackson Immunoresearch) at 3.1 µg/ml for 40 minutes at room temperature. Panels labeled Cy3 and GFP show location of clusters expressing HA-GST and GFP, respectively. Merged panel shows superimposition of Cy3 and GFP signals and yellow color indicates co-expression. Scale bar equals 100 µm.

FIG. 4F is an enlarged view of boxed area of scan image from FIG. 4E.

DETAILED DESCRIPTION OF THE INVENTION

Figure 1:
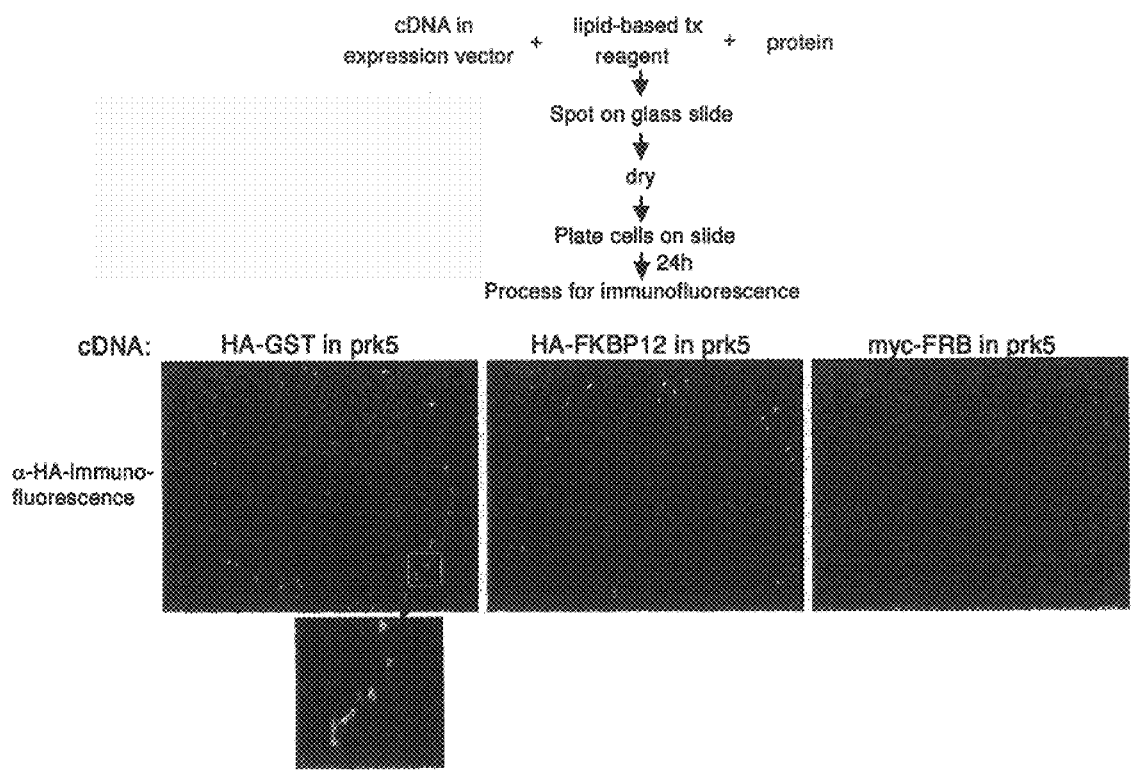
FIG. 1 is a schematic representation of one embodiment of the present method of reverse transfection, in which cDNA (HA-GST, HA-FKBP12 or myc-FRB) in an expression vector (prk5) was introduced into cells by the following procedures: combining cDNA in an expression vector, a lipid-based transfection reagent and a carrier protein, to produce a mixture; spotting the mixture onto a glass slide; allowing the spotted mixture to dry on the slide surface; plating human embryonic kidney (HEK 293T) cells into which cDNA is to be introduced onto the slide; maintaining the resulting slide under conditions appropriate for reverse transfection to occur; and detecting immunofluorescence using a fluorescently labeled antibody that binds HA but not myc, demonstrating the presence and location of expressed cDNA.
Figure 2:
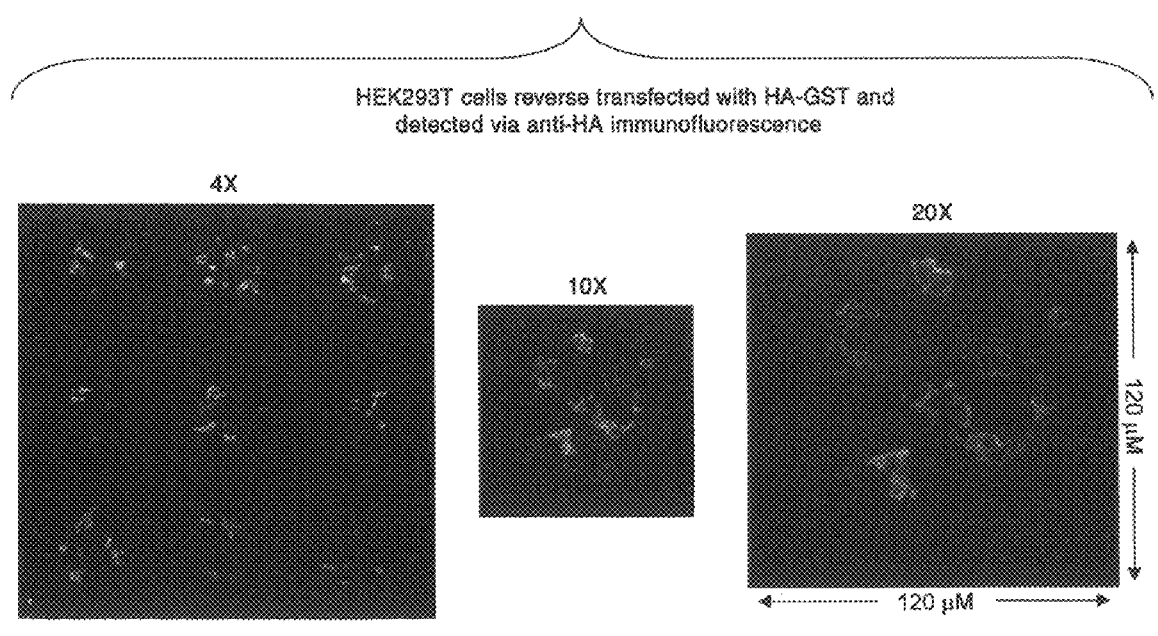
FIG. 2 shows the results of reverse transfection of HEK293T cells with HA-GST, as demonstrated using anti-HA imunofluorescence.
Figure 3:
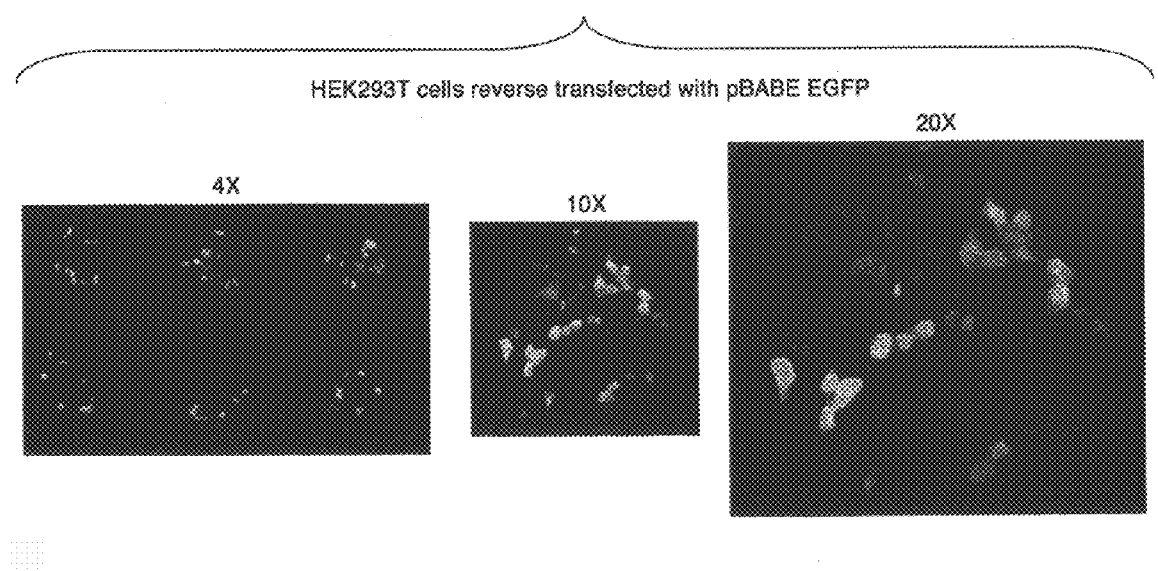
FIG. 3 shows the results of reverse transfection of HEK293T cells with pBABE EGFP, as demonstrated by detecting endogenous fluorescence of EGFP.

A microarray-based system was developed to analyze the function in mammalian cells of many genes in parallel. Mammalian cells are cultured on a glass slide printed in defined locations with solutions containing different DNAs. Cells growing on the printed areas take up the DNA, creating spots of localized transfection within a lawn of non-transfected cells. By printing sets of complementary DNAs (cDNAs) cloned in expression vectors, micoarrays which comprise groups of live cells that express a defined cDNA at each location can be made. Transfected cell microarrays can be of broad utility for the high-throughput expression cloning of genes, particularly in areas such as signal transduction and drug discovery. For example, as shown herein, transfected cell microarrays can be used for the unambiguous identification of the receptor for the immunosuppressant FK506 and components of tyrosine kinase pathways.

The present invention relates to a method of introducing defined DNAs into cells at specific discrete, defined locations on a surface by means of a reverse transfection method. That is, the present method makes use of DNAs, of known sequence and/or source, affixed to a surface (DNA spots), such as a slide or well bottom, and growing cells that are plated onto the DNA spots and maintained under conditions appropriate for entry of the DNAs into the cells. The size of the DNA spots and the quantity (density) of the DNA spots affixed to the surface can be adjusted depending on the conditions used in the methods. For example, the DNA spots can be from about 100 µm to about 200 µm in diameter and can be affixed from about 200 µm to about 500 µm apart on the surface. The present method further includes identification or detection of cells into which DNA has been reverse transfected. In one embodiment, DNA introduced into cells is expressed in the cells, either by an expression vector containing the DNA or as a result of integration of reverse transfected DNA into host cell DNA, from which it is expressed. In an alternative embodiment of the present method, DNA introduced into cells is not expressed, but affects cell components and/or function itself. For example, antisense DNA can be introduced into cells by this method and affect cell function. For example, a DNA fragment which is anti-sense to an mRNA encoding a receptor for a drug can be introduced into cells via reverse transfection. The anti-sense DNA will decrease the expression of the drug receptor protein, causing a decrease in drug binding to cells containing the anti-sense DNA. In the method, a mixture comprising DNA of interest (such as cDNA or genomic DNA incorporated in an expression vector) and a carrier protein is deposited (e.g., spotted or placed in small defined areas) onto a surface (e.g., a slide or other flat surface, such as the bottoms of wells in a multi-welled plate) in defined, discrete (distinct) locations and allowed to dry, with the result that the DNA-containing mixture is affixed to the surface in defined discrete locations.

Detection of effects on recipient cells (cells containing DNA introduced by reverse transfection) can be carried out by a variety of known techniques, such as immunofluorescence, in which a fluorescently labeled antibody that binds a protein of interest (e.g., a protein thought to be encoded by a reverse transfected DNA or a protein whose expression or function is altered through the action of the reverse transfected DNA) is used to determine if the protein is present in cells grown on the DNA spots.

The nucleic acid used in the methods of the present invention can be oligonucleotides, DNA and/or RNA. The nucleic acid of interest introduced by the present method can be nucleic acid from any source, such as nucleic acid obtained from cells in which it occurs in nature, recombinantly produced nucleic acid or chemically synthesized nucleic acid. For example, the nucleic acid can be cDNA or genomic DNA or DNA synthesized to have the nucleotide sequence corresponding to that of naturally-occurring DNA. The nucleic acid can also be a mutated or altered form of nucleic acid (e.g., DNA that differs from a naturally occurring DNA by an alteration, deletion, substitution or addition of at least one nucleic acid residue) or nucleic acid that does not occur in nature. Nucleic acid introduced by the subject method can be present in a vector, such as an expression vector (e.g., a plasmid or viral-based vector), but it need not be. Nucleic acid of interest can be introduced into cells in such a manner that it becomes integrated into genomic DNA and is expressed or remains extrachromosomal (is expressed episomally). The nucleic acid for use in the methods of the present invention can be linear or circular and can be of any size. For example, the nucleic acid can be from about 3 kb to about 10 kb, from about 5 kb to about 8 kb and from about 6 kb to 7 kb. Nucleic acid introduced into cells by the method described herein can further comprise nucleic acid (e.g., DNA) that facilitates entry of the nucleic acid into cells or passage into the cell nucleus (nuclear localization elements).

The carrier for use in the methods of the present invention can be, for example, gelatin or an equivalent thereof.

Eukaryotic cells, such as mammalian cells (e.g., human, monkey, canine, feline, bovine, or murine cells), bacterial, insect or plant cells, are plated (placed) onto the surface bearing the DNA-containing mixture in sufficient density and under appropriate conditions for introduction/entry of the DNA into the eukaryotic cells and expression of the DNA or its interaction with cellular components. Preferably, the eukaryotic cells (in an appropriate medium) are plated on top of the dried DNA-containing spots at high density (e.g., $0.5-1\times10^5/cm^2$), in order to increase the likelihood that reverse transfection will occur. For example, the density of cells can be from about $0.3\times10^5/cm^2$ to about $3\times10^5/cm^2$, and in specific embodiments, is from about $0.5\times10^5/cm^2$ to about $2\times10^5/cm^2$ and from about $0.5\times10^5/cm^2$ to about $1\times10^5/cm^2$. The appropriate conditions for introduction/entry of DNA into cells will vary depending on the quantity of cells used.

Two embodiments of the present method are described in detail herein: a DNA-gelatin method, in which a mixture comprising DNA (e.g., DNA in an expression vector, such as, a plasmid-based or viral-based vector) and a carrier protein (e.g., gelatin) is used and a lipid vector-DNA method, in which a mixture comprising DNA, such as DNA in an expression vector (e.g., a plasmid); a carrier protein (e.g., gelatin); a sugar (e.g., sucrose); DNA condensation buffer; and an appropriate lipid-containing transfection reagent is used. Any suitable gelatin which is non-toxic, hydrated, which can immobilize the nucleic acid mixture onto a surface and which also allows the nucleic acid immobilized on the surface to be introduced over time into cells plated on the surface can be used. For example, the gelatin can be a crude protein gelatin or a more pure protein based gelatin such as fibronectin. In addition, a hydrogel, a sugar based gelatin (polyethylene glycol) or a synthetic or chemical based gelatin such as acrylamide can be used.

In the first embodiment, a mixture comprising two components (DNA such as DNA in an expression vector and a carrier protein) is spotted onto a surface (e.g., a slide) in discrete, defined locations or areas and allowed to dry. One example of this embodiment is described in Example 1. After the carrier (e.g., gelatin)-DNA mixture has dried sufficiently that it is affixed to the surface, transfection reagents (a lipofection mixture) and cells to be reverse transfected are added, preferably sequentially. The transfection mixture can be one made from available components or can be a commercially available mixture, such as Effectene™ (Qiagen), Fugene™ 6 (Boehringer Mannheim) or Lipofectamine™ (Gibco/BRL-Life Technologies). It is added in an appropriate quantity, which can be determined empirically, taking into consideration the amount of DNA in each defined location. A wax barrier can be drawn around the locations on the surface which contain the vector-DNA mixture, prior to addition of the transfection mixture, in order to retain the mixture or the solution can be kept in place using a cover well. Generally, in this embodiment, the transfection reagent is removed, such as by vacuum suctioning, prior to addition of cells into which DNA is to be reverse transfected. Actively growing cells are plated on top of the locations, producing a surface that bears the DNA-containing mixture in defined locations. The resulting product is maintained under conditions (e.g., temperature and time) which result in entry of DNA in the DNA spots into the growing cells. These conditions will vary according to the types of cells and reagents used and can be determined empirically. Temperature can be, for example, room temperature or 37° C., 25° C. or any temperature determined to be appropriate for the cells and reagents.

A variety of methods can be used to detect protein expression in the DNA-containing spots. For example, immunofluorescence can be used to detect a protein. Alternatively, expression of proteins that alter the phosphorylation state or subcellular localization of another protein, proteins that bind with other proteins or with nucleic acids or proteins with enzymatic activity can be detected.

In the second embodiment, one example of which is described in Example 2, a mixture comprising DNA in an expression vector; a carrier protein (e.g., gelatin); a sugar (e.g., sucrose); DNA condensation buffer; and a lipid-based transfection reagent is spotted onto a surface, such as a slide, in discrete, defined locations and allowed to dry. Actively growing cells are plated on top of the DNA-containing locations and the resulting surface is maintained under conditions (e.g., temperature and time) which result in entry of DNA in the DNA spots into the growing cells (reverse transfection). Expression of DNA in cells is detected using known methods, as described above.

Any suitable surface which can be used to affix the DNA containing mixture to its surface can be used. For example, the surface can be glass, polystyrene or plastic. In addition, the surface can be coated with, for example, polylysine.

The present invention also encompasses methods of making arrays which comprise DNA affixed to a surface such that when cells are plated onto the surface bearing the DNA, the DNA can be introduced (is introducible) into the cells (i.e., the DNA can move from the surface into the cells). The present invention also encompasses a DNA array comprising a surface having affixed thereto, in discrete, defined locations, DNA of known sequence or source by a method described herein.

The methods of this invention are useful to identify DNAs of interest (DNAs that are expressed in recipient cells or act upon or interact with recipient cell constituents or function, such as DNAs that encode a protein whose function is desired because of characteristics its expression gives cells in which it is expressed). They can be used in a variety of formats, including macro-arrays and micro-arrays. They permit a DNA array to be converted into a protein or cell array, such as a protein or cell microarray.

The present invention is illustrated by the following examples, which are not intended to be limiting in any way.

EXAMPLE 1

Reverse Transfection: "Gelatin-DNA" Method

Materials

[DNA]: 1 μg/μL (eg., HA-GST pRK5, pBABE CMV GFP)

Gelatin (ICN, cat.#901771): 0.2% stock in ddH$_2$O, all dilutions made in PBS$^-$ 0.20% gelatin=0.5

Effectene Transfection Kit (Qiagen, cat.#301425)

Plasmid-DNA: grown in 100 mL L-amp overnight from glycerol stock, purified by standard Qiaprep Miniprep or Qiagen Plasmid Purification Maxi protocols Cell Type: HEK 293T cultured in DMEM/10% IFS with L-glut and pen/strep Diluting and Spotting DNA Dilute DNA in 0.2% gelatin* to give final [DNA]=0.05μg/μL**

Spot DNA/gelatin mix on Σ poly-L-lysine slides using arrayer

Allow slides to dry in vacuum-dessicator overnight***
range of gelatin concentration that worked under the conditions used=0.05% to 0.5%
range of DNA concentrations that worked under the conditions used=0.01 μg/μl to 0.1 μg/μl
range of drying time=2 hours to 1 week Adding Tx. Reagents to Gelatin-DNA Spots In eppendorf tube, mix 300 μL DNA-condensation buffer (EC Buffer)+16 μL Enhancer Mix by vortexing. Incubate for 5 minutes Add 50 μL Effectene and mix by pipetting Draw a wax circular barrier on slide around spots to apply the transfection reagent Add 366 μL mix to wax-enclosed region of spots Incubate at room temperature for 10 to 20 minutes Meanwhile, split cells to reverse-transfect Vacuum-suction off reagent in hood Place Slides in Dish and Add Cells for Reverse Transfection Splitting Cells Split actively growing cells to [cell]=10$^7$ cells in 25 mL Plate cells on top of slide(s) in square 100×100×15 mm petri dish Allow reverse transfection to proceed for 40 hours= approx. 2 cell cycles Process slides for immunofluorescence

EXAMPLE 2

Reverse Transfection: "Lipid-DNA" Method

Materials

[DNA]: 1 μg/μL (eg., HA-GST pRK5, pBABE CMV GFP)

Gelatin (ICN, cat.#901771): 0.2% stock in ddH$_2$O, all dilutions made in PBS$^-$ 0.05% gelatin=250

Effectene Transfection Kit (Qiagen, cat.#301425):
EC Buffer in 0.4M sucrose=273.6 μL 50% sucrose+ 726.4 μL EC Buffer Plasmid-DNA: grown in 100 mL L-amp overnight from glycerol stock, purified by standard Qiaprep Miniprep or Qiagen Plasmid Purification Maxi protocols Cell Type: HEK 293T cultured in DMEM/10% IFS with L-glut and pen/strep Reverse Transfection Protocol with Reduced Volume Aliquot 1.6 μg DNA in separate eppendorf tubes Add 15 μL of pre-made DNA-condensation buffer (EC Buffer) with 0. 4M sucrose* to tubes Add 1.6 μL of Enhancer solution and mix by pipetting several times. Incubate at room temperature for 5 minutes Add 5 μL of Effectene Transfection Reagent to the DNA-Enhancer mix and mix by pipetting. Incubate at room temperature for 10 minutes Add 23.2 μL of 0.05% gelatin** to total transfection reagent mix (i.e. 1:1 dilution)

Spot lipid-DNA on Σ poly-L-lysine slides mix using arrayer

Allow slides to dry in vacuum-dessicator overnight***
Effectene™ kit (Qiagen) used includes Enhancer solution, which was used according to Qiagen's instructions.
range of sucrose that worked under the conditions used= 0.1M to 0.4M
range of gelatin concentration that worked under the conditions used=0.01% to 0.05%
range of drying time=2 hours to 1 week Splitting Cells Split actively growing cells to [cell]=10$^7$ cells in 25 mL Plate cells on top of slide(s) in square 100×100×15 mm petri dish Allow reverse transfection to proceed for 40 hours= approx. 2 cell cycles Process slides for immunofluorescence

EXAMPLE 3

Transfected Cells Micorarrays: A Genomics Approach for the Analysis of Gene Products in Mammalian Cells Lipid-DNA Method I. Gelatin Preparation and DNA Purification Materials:

Gamma-Amino Propyl Silane (GAPS) slides (Corning catalog #2550),

Purified cDNA,

Gelatin, Type B: 225 Bloom (Sigma, catalog #G-9391),

Methods:

0.2% Gelatin was made by incubation in a 60° C. water bath for 15 minutes. The gelatin was cooled slowly to 37° C. at which point it was filtered through 0.45 μm cellular acetate membrane (CA).

Bacterial clones with DNA plasmids were grown in a 96 Deep-Well Dish for 18 to 24 hours in 1.3 mL of terrific broth (TB) shaking at 250 rpm at 37° C. The plasmids were miniprepped and optical density (OD) was taken. DNA purity, as indicated by final 280 nm/260 nm absorbance ratio, was greater than 1.7.

Storage:

For storage purposes, gelatin was kept at 4° C. and miniprepped DNA kept at −20° C.

II. Sample Preparation and Array Printing

Materials:

Effectene Transfection Reagent (Qiagen catalog #301425),

Sucrose (Life Technologies),

INTEGRID 100 mm×15 mm Tissue Culture Square Petri Dishes (Becton Dickinson: Falcon catalog #35-1012), Costar 384-well plates (VWR catalog #7402), Stealth Micro Spotting Pins, (Telechem International, Inc. catalog #SMP4), PixSys 5500 Robotic Arrayer (Cartesian Technologies, Model AD20A5), Vacuum Dessicator with Stopcock 250 mm, NALGENE (VWR catalog #24987-004), DRIERITE Anhydrous Calcium Sulfate (VWR catalog #22890-229)

Forceps to hold slides,

Human Embryonic Kidney (HEK) 293T cells,

Tissue Culture hood,

Cover Slips (50 mm×25 mm),

Methods:

For each DNA-containing spot, 15 µl of pre-made DNA-condensation buffer (Buffer EC) with 0.2M to 0.4M sucrose was added to 0.80 µg to 1.60 µg DNA in a separate eppendorf tube. Subsequently, 1.5 µl of the Enhancer solution was added to the tube and mixed by pipetting. This was let to incubate at room temperature for 5 minutes. 5 µl Effectene transfection reagent was added, mixed and let to incubate at room temperature for 10 minutes with the DNA-Enhancer mixture. 1×volume of 0.05% gelatin was added, mixed and the appropriate amount was aliquoted into a 384-well plate for arraying purposes.

The PixSys 5500 Robotic Arrayer was used with Telechem's Arraylt Stealth Pins (SMP4) with each spot spaced 400 µm apart with a 50 ms to 500 ms delay time of the pin on the slide for each spot. A 55% relative humidity environment was maintained during the arraying. A thorough wash step was implemented between each dip into a DNA sample in the 384-well plate to avoid clogging of the pins that would result in missing spots in the array.

In a tissue culture hood, $10 \times 10^6$ Human Embryonic Kidney (HEK) 293T cells were prepared in 25 ml DME media with 10% IFS, pen/strep and glutamine for every 3 slides that were to be processed. After arraying, the slides were simply placed array-side facing up on a sterile 100× 100×10 mm square dish (3 slides per plate) and the cells were poured gently on the slides while avoiding direct pouring on the arrays themselves. If the number of slides were not a multiple of 3, dummy slides were placed to cover the square dish.

The cells were let to grow on the arrays for approximately 2 cell cycles (~40 hours for 293T). Subsequently, the slides were very gently rinsed with PBS⁻ in a Coplin jar, and then fixed in 3.7% paraformaldehyde/4.0% sucrose for 20 minutes in a Coplin jar, and then transferred back to a jar with PBS⁻.

Storage:

After arraying, slides were stored at room temperature in a vacuum dessicator with anhydrous calcium sulfate pellets. After fixation, slides were kept in PBS⁻ at 4° C. until analyses were completed (maximum of 5 days).

III. Methods of Detection

Immunofluorescence

Fluorescence Microscopy

Laser Scanning

Radiolabelling and detection with sensitive film or emulsion

If the expressed proteins to be visualized are fluorescent proteins, they can be viewed and photographed by fluorescent microscopy. For large expression array, slides may be scanned with a laser scanner for data storage. If a fluorescent antibody can detect the expressed proteins, the protocol for immunofluorescence can be followed. If the detection is based on radioactivity, the slides can be fixed as indicated above and radioactivity detected by autoradiography with film or emulsion.

Immunofluorescence:

After fixation, the array area was permeabilized in 0.1% Triton X-100 in PBS⁻ for 15 minutes. After two rinses in PBS⁻, the slides were blocked for 60 minutes, probed with a primary antibody at 1:200 to 1:500 dilution for 60 minutes, blocked for 20 minutes, probed with a fluorescent secondary antibody at 1:200 dilution for 40 minutes. The slides can be transferred to a Coplin jar in PBS⁻ and visualized under an upright fluorescent microscope. After analyses, the slides can be mounted and stored in the dark at 4° C.

Figure 4A:
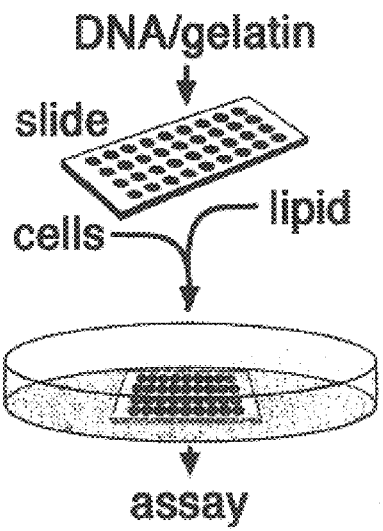
FIG. 4A is a schematic for making transfected cell microarrays using a well-less transfection of plasmid DNAs in defined areas of a lawn of mammalian cells. Plasmid DNA dissolved in an aqueous gelatin solution is printed on a glass slide using a robotic arrayer. The slide is dried and the printed array covered with a lipid transfection reagent. After removal of the lipid, the slide is placed in a culture dish and covered with cells in media. The transfected cell microarray forms in 1–2 days and is then ready for downstream assays. An alternative method in which the lipid is added to the DNA/gelatin solution prior to printing is also described.

To create these microarrays, distinct and defined areas of a lawn of cells were simultaneously transfected with different plasmid DNAs (FIG. 4A). This is accomplished without the use of individual wells to sequester the DNAs. Nanoliter volumes of plasmid DNA in an aqueous gelatin solution are printed on a glass slide. A robotic arrayer (PixSys 5500, Cartesian Technologies) equipped with stealth pins (SMP4, Telechem) was used to print a plasmid DNA/gelatin solution contained in a 384-well plate onto CMT GAPS glass slides (Corning). The pins deposited ~1 nl volumes 400 µm apart using a 25 ms pin down slide time in a 55% relative humidity environment. Printed slides were stored at room temperature in a vacuum desiccator until use. Preparation of aqueous gelatin solution is important and is as follows. 0.02% gelatin (w/v) (Sigma G-9391) was dissolved in MilliQ water by heating and gentle swirling in a 60° C. water bath for 15 minutes. The solution was cooled slowly to room temperature and filtered through a 0.45 µm cellular acetate membrane and stored at 4° C. Plasmid DNA was purified with the Plasmid Maxi or QIAprep 96 Turbo Miniprep kits (Qiagen), and always had an A260/A280>1.7. Concentrated solutions of DNA were diluted in the gelatin solution so to keep the gelatin concentration >0.017% and, unless otherwise specified, final plasmid DNA concentrations were 0.033 µg/µl. To express GFP the EGFP construct in pBABEpuro was used.

After drying, the DNA spots are briefly exposed to a lipid transfection reagent, the slide is placed in a culture dish and covered with adherent mammalian cells in media. The Effectene transfection kit (301425, Qiagen) was used as follows. In a 1.5 ml microcentrifuge tube, 16 µl enhancer was added to 150 µl EC buffer, mixed, and incubated for 5 minutes at room temperature. 25 µl effectene lipid was added, mixed and the entire volume pipetted onto a 40×20 mm cover well (PC200, Grace Bio-Labs). A slide with the printed side down was placed on the cover well such that the solution covers the entire arrayed area while also creating an airtight seal. After a 10 minute incubation, the cover well was pried off the slide with a forceps and the transfection reagent removed carefully by vacuum aspiration. The slide was placed printed side up in a 100×100×10 mm square tissue culture dish and a $1 \times 10^7$ actively growing HEK293T cells in 25 ml media (DMEM with 10% FBS, 50 units/ml penicillin and 50 µ/ml streptomycin) were poured into the dish. Three slides can be transfected side-by-side in this fashion. The cells grew on the slide for 40 hours prior to fixing for 20 minutes at room temperature in 3.7% paraformaldehyde/4.0% sucrose in PBS. Other commonly used mammalian cells lines, such as HeLa and A549 cells, were also tested and similar results were obtained but with transfection efficiencies of 30–50% of those obtained with HEK293 cells. The DNA in the gelatin gel is insoluble in cell culture media but readily enters cells growing on it to create the transfected cell microarray.

To illustrate the method, an array with elements containing an expression construct for the green fluorescent protein (GFP) was printed. HEK293 cells were plated on the slide for transfection and the fluorescence of the cells detected with a laser fluorescence scanner. Microarrays were imaged at a resolution of 5 µm with a laser fluorescence scanner (ScanArray 5000, GSI Lumonics). GFP and cy3 emission was measured separately after sequential excitation of the two fluorophores. To obtain images at cellular resolution, cells were photographed with a conventional fluorescent microscope. All images were pseudocolored and superimposed using Photoshop 5.5 (Adobe Systems).

Figure 4B:
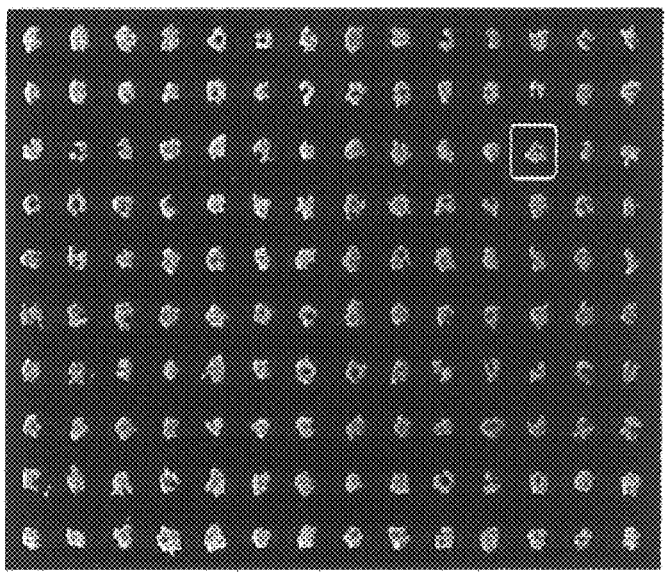
FIG. 4B is a GFP-expressing microarray made from a slide printed in a 12×8 pattern with a GFP expression construct.
Figure 4C:
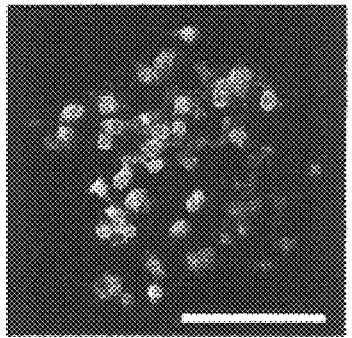
FIG. 4C is a higher magnification image obtained with fluorescence microscopy of the cell cluster boxed in FIG. 4B. Scale bar equals 100 $\mu$m.

A low magnification scan showed a regular pattern of fluorescent spots that matches the pattern in which the GFP expression construct was printed (FIG. 4B). A higher magnification image obtained via fluorescence microscopy showed that each spot is about 150 µm in diameter and consists of a cluster of 30–80 fluorescent cells (FIG. 4C). As in a conventional transfection, the total expression level in the clusters is proportional over a defined range to the amount of plasmid DNA used (FIG. 4D). Since it may be useful to express two different plasmids in the same cells, whether the technique is compatible with cotransfection was examined. Arrays with elements containing expression constructs for GFP, an epitope-tagged protein or both were prepared and transfected. The cells growing on elements printed with both cDNAs express both encoded proteins, indicating that cotransfection had occurred (FIG. 4E).

Figure 5A:
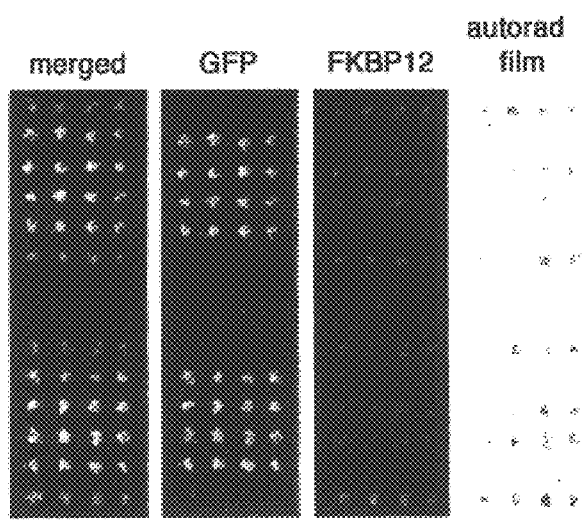
FIG. 5A is a laser scan showing detection of the receptor for FK506. Arrays with elements containing expression constructs for GFP, myc-FKBP 12 or both were printed and transfected with HEK293 cells. 5 nM dihydro-FK506 [propyyl-$^3$H] (NEN) was added to the culture media 1 hour prior to fixation and processing for immunofluorescence and autoradiography. Slides were process for anti-myc immunofluorescence, scanned at 5 µm resolution and photographed using a fluorescent microscope, and then exposed to tritium sensitive film (Hyperfilm, Amersham) for 4 days. Autoradiographic emulsion was performed as described by the manufacturer (Amersham). Laser scans show expression pattern of GFP and FKBP12 and superimposition of both (merged). Film autoradiography detects binding of tritiated FK506 to the same array (autorad film).
Figure 5B:
FIG. 5B is a higher magnification image obtained by fluorescent microscopy of an FKBP 12-expressing cluster (FKBP12). Emulsion autoradiography detects, with cellular resolution, binding of tritiated FK506 to the same cluster (autorad emulsion).

Whether transfected cell microarrays could be used to clone gene products based on their intrinsic properties was also determined. As a test case, an array to identify the receptor for FK506, a clinically important immunosuppressant whose pharmacologically relevant target, FKBP12, is an intra-cellular protein, was used (Kino, T., et al., *J. Antiobiot.*, 40:1256 (1987); Harding, M. W., et al., *Nature*, 26:755 (1989)). Elements containing expression constructs for FKBP12, GFP, or both were printed on a slide, in an easily recognizable pattern. After the transfected cell microarray formed, radiolabeled FK506 was added to the tissue culture media for one hour prior to processing the slide for autoradiography and immunofluorescence. The radiolabeled FK506 bound to the array in a pattern of spots that exactly matches the pattern of cell clusters expressing FKBP12 (FIG. 5A). Detection of the bound FK506 with autoradiographic emulsion confirmed, at the cellular level, colocalization between FKBP12 expression and FK506 binding (FIG. 5B). The binding is specific because the GFP-expressing clusters and the non-transfected cells surrounding the clusters showed only background levels of signal (FIG. 5A). Furthermore, the prior addition of excess rapamycin, a competitive antagonist of FK506, completely eliminated the signal. 1 µM rapamycin was added to the cell culture media 30 minutes before the addition of radiolabeled FK506.

The utility of transfected cell microarrays for identifying gene products that induce phenotypes of interest in mammalian cells or have a distinct sub-cellular localization was also explored. Arrays with a collection, enriched for signaling molecules, of 192 distinct epitope-tagged cDNAs in expression vectors were printed. 192 Genestrom expression constructs (Invitrogen) in bacteria were cultured in two 96-well plates and plasmid DNA was purified using the Turbo Miniprep Kit (Qiagen). Plasmid DNA was diluted with 0.02% gelatin to a final concentration of 0.040 µg/µl and printed. Cellular phosphotyrosine levels were determined by immunofluorescence staining and scanning. Cell morphology and subcellular localization of expressed proteins was assessed by visual inspection via fluorescence microscopy of the cells in the clusters after their detection with anti-V5 immunofluorescence.

Figure 5C:
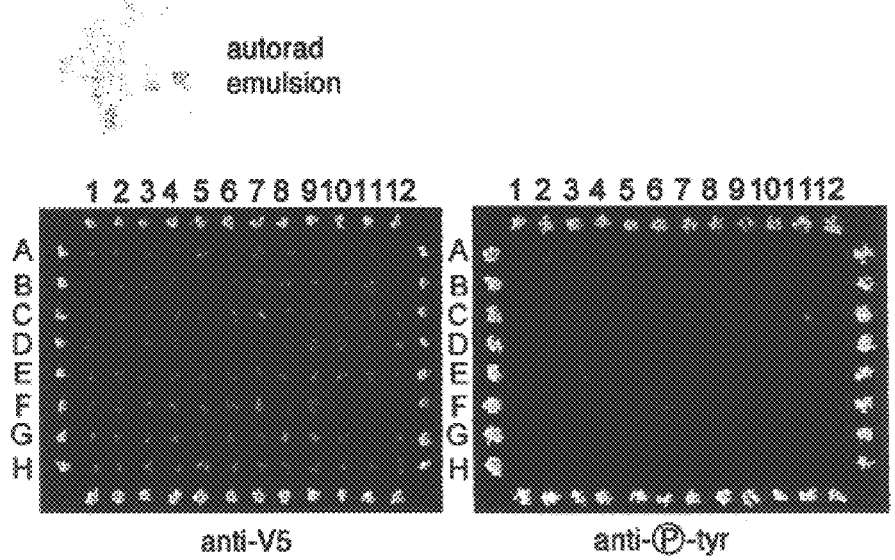
FIG. 5C is a scan showing detected components of tyrosine kinase signaling cascades. 192 V5-epitope-tagged cDNAs in expression vectors were printed in two 8×12 subgrids named array 1 and 2. For ease of determining the coordinates of cell clusters within the arrays a border around each array was printed with the GFP expression construct. After transfection, separate slides were processed for anti-V5 or anti-phosphotyrosine immunofluorescence and Cy3 and GFP fluorescence detected. Merged images of array 1 show location of clusters expressing V5-tagged proteins (left panel) and having increased levels of phosphotyrosine (right panel). No DNA was printed in coordinates F10–12.
Figure 5D:
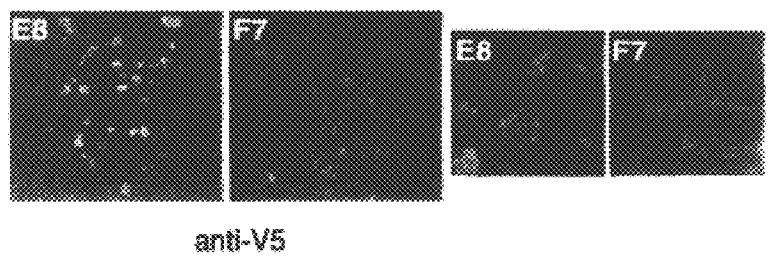
FIG. 5D show two examples of the morphological phenotypes detectable in the transfected cell microarrays described in FIG. 5C. Clusters shown are E8 and F7 from array 2.

After transfection, their effects on cellular phosphotyrosine levels and morphology as well as their subcellular localization were determined. Five cell clusters on grid 1 (A2, C7, C9, C11, and F6) had phosphotyrosine levels above background (FIG. 5C). The coordinates of the clusters match those of the wells of a microtiter plate containing the source cDNAs and were used to look up the identity of the transfected cDNAs. This revealed that four of these clusters were transfected with known tyrosine kinases (trkC, syk, syn, and blk) while the fifth (C11) encodes a protein of unknown function. Simple visual examination of the morphology of the cells in the transfected clusters revealed a diversity of cellular phenotypes even in this small set of clones. In array 2, cluster E8 had fragmented cells characteristic of apoptosis while in two clusters (D10 and F7) the cells were closely attached to each other (FIG. 5D). The presence of apoptotic cells was confirmed by TUNEL (Terminal deoxynucleotidyl transferase mediated dUTP-biotin nick end labeling method) staining. TUNEL staining was performed as described (Y. Gavrieli, Y. Sherman, S. A. Ben-Sasson. J. Cell Biol. 119, 493 (1992)).

The observed phenotypes are consistent with the presumed functions of the cDNAs expressed in these clusters (the Table). Subcellular localization of the expressed proteins were examined through visual inspection the and those with distinct patterns were noted (the Table). This revealed that several proteins that are known transcription factors were mainly located in the cell nucleus. This was also true for other proteins, such as phosphatase 1-beta, whose subcellular distribution has not been previously ascertained.

TABLE

Description of selected cDNAs expressed in the transfected cell microarray. Shown are the coordinates, the phenotype or property detected, the Genbank accession number and the name of the cDNA. nuc/cyto means nuclear and cytoplasmic staining was visible.

| Grid: Coordinate | Phenotype/ property | Accession number | Function |
| --- | --- | --- | --- |
| 2:E8 | apoptosis | AF016266 | TRAIL receptor 2 |
| 2:D10 | cell adhesion | X97229 | NK receptor |
| 2:F7 | cell adhesion | M98399 | CD36 |
| 1:A9 | nuclear | U11791 | Cyclin H |
| 1:B5 | nuclear | M60527 | deoxycytidine kinase |
| 1:B12 | nuclear | M60724 | p70 S6 kinase kinase α1 |
| 1:C12 | nuclear | M90813 | D-type cyclin |
| 1:E4 | mitochondrial | U54645 | methylmalonyl-coA mutase |
| 1:E10 | mitochondrial | J05401 | creatine kinase |
| 1:G9 | nuc/cyto | U40989 | tat interactive protein |
| 1:G10 | nuc/cyto | U09578 | MAPKAP (3pk) kinase |
| 2:A9 | nuclear | X83928 | TFIID subunit TAFII28 |
| 2:A12 | nuc/cyto | M62831 | ETR101 |
| 2:B6 | nuc/cyto | X06948 | IgE receptor α-subunit |
| 2:B12 | nuclear | X63469 | TFIIE β subunit |
| 2:C5 | nuclear | M76766 | General transcription factor IIB |
| 2:C7 | nuc/cyto | M15059 | CD23A |
| 2:C12 | nuclear | X80910 | PP1, β catalytic subunit |
| 2:D4 | nuclear | AF017307 | Ets-related transcription factor |
| 2:E7 | nuclear | X63468 | TFIIE α |
| 2:E12 | nuclear | U22662 | Orphan receptor LXR-α |
| 2:F8 | nuclear | L08895 | MEF2C |
| 2:F12 | nuclear | AF028008 | SP1-like transcription factor |
| 2:G2 | nuc/cyto | U37352 | PP2A, regulatory B' α 1 subunit |
| 2:G3 | nuc/cyto | L14778 | PP2B, catalytic α subunit |

The microarrays can be printed with the same robotic arrayers as traditional DNA arrays, so it is feasible to achieve densities of up 10,000–15,000 cell clusters per standard slide. At these densities the entire set of human genes can be expressed on a small number of slides, allowing rapid pan-genomic screens. Thus, comprehensive collections of full-length cDNAs for all mammalian genes can be generated (Strausberg, R. L., et al., Science, 15:455 (1999) and will be valuable tools for making such arrays.

Transfected cell microarrays have distinct advantages over conventional expression cloning strategies using FACs or sib selection (Simonsen, H., et al., *Ttrends Pharmacol. Sci.*, 15:437 (1994)). First, cDNAs do not need to be isolated from the cells exhibiting the phenotype of interest. This allows for screens using a variety of detection methods, such as autoradiography or in situ hybridization, and significantly accelerates the pace of expression cloning. The experiments described herein took days to perform instead of the weeks to months necessary with other expression cloning strategies. Second, transfected cell microarrays can also be used to screen living cells, allowing the detection of transient phenotypes, such as changes in intracellular calcium concentrations. Third, being compact and easy to handle, transfected cell microarrays have economies of scale. The arrays are stable for months and can be printed in large numbers, allowing many phenotypes to be screened in parallel, with a variety of methods, in a small number of tissue culture plates.

Described herein are arrays in which the transfected plasmids direct gene overexpression. However, as antisense technology improves or other methods emerge for decreasing gene function in mammalian cells, it is likely that transfected cell microarrays can be used to screen for phenotypes caused by loss of gene function. Lastly, the immobilization of the plasmid DNA in a degradable gel is the key to spatially restricting transfection without wells.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of introducing nucleic acid molecules into mammalian cells comprising:
   (a) depositing a plurality of nucleic acid molecule-containing mixtures onto a surface in discrete, defined locations, wherein each of the nucleic acid molecule-containing mixtures comprises a nucleic acid molecule to be introduced into mammalian cells and a gelatin;
   (b) allowing the nucleic acid molecule-containing mixtures to dry on the surface, thereby producing a surface having the nucleic acid molecule-containing mixtures affixed thereon in discrete, defined locations; and
   (c) plating the mammalian cells onto the surface at a density of $0.3 \times 10^5/cm^2$ to $3.0 \times 10^5/cm^2$ under appropriate conditions for entry of the nucleic acid molecules in the nucleic acid molecule-containing mixtures into mammalian cells; whereby the nucleic acid molecules are introduced into the mammalian cells in the location in which each of the nucleic acid molecule-containing mixtures was deposited.

2. The method of claim 1, further comprising the steps after step (b) of:
   (i) covering the surface bearing the nucleic acid molecule-containing mixtures with an appropriate amount of a lipid-based transfection reagent and maintaining the resulting product under conditions appropriate for complex formation between the nucleic acid molecules in the nucleic acid molecule-containing mixture and the transfection reagent; and
   (ii) removing the non-complexed transfection reagent.

3. The method of claim 1, wherein said nucleic acid molecule-containing mixtures further comprise a sugar, a buffer that facilitates nucleic acid molecule condensation, and an appropriate lipid-based transfection reagent.

4. The method of any one of claims 1–3, wherein each nucleic acid molecule to be introduced is contained in a vector.

5. The method of claim 4, wherein the vector is an episomal vector or a chromosomally integrated vector.

6. The method of claim 4, wherein the vector is a plasmid or a viral-based vector.

7. The method of claim 6, wherein the vector is an expression vector.

8. The method of claim 7, wherein said nucleic acid molecules are expressed in the mammalian cells.

9. The method of any one of claims 1–3, wherein the surface is glass, polystyrene or plastic, optionally coated with poly-L-lysine.

10. The method of any one of claims 1–3, wherein the surface is the surface of a slide.

11. The method of claim 10, wherein the slide is a glass slide coated with poly-L-lysine or a gamma-amino propyl silane slide.

12. The method of any one of claims 1–3, wherein the cells are plated at a density of $0.5 \times 10^5/cm^2$ to $2.0 \times 10^5/cm^2$.

13. The method of claim 12, wherein the cells are plated at a density of $0.5 \times 10^5/cm^2$ to $1.0 \times 10^5/cm^2$.

14. The method of any one of claims 1–3, wherein said nucleic acid molecule is an oligonucleotide, DNA, or RNA.

15. The method of claim 14, wherein said nucleic acid molecule is DNA.

16. The method of claim 1 or 2, wherein said nucleic acid molecule is DNA and wherein the concentration of said DNA is 0.01 $\mu g/\mu l$ to 0.5 $\mu g/\mu l$.

17. The method of claim 15, wherein the concentration of said DNA is 0.02 $\mu g/\mu l$ to 0.1 $\mu g/\mu l$.

18. The method of claim 3, wherein said nucleic acid molecule is DNA and wherein the concentration of said DNA is 0.1 $\mu g/\mu l$ to 2.0 $\mu l/\mu l$.

19. The method of any one of claims 1–3, wherein said nucleic acid molecules encode polypeptides that are expressed in the mammalian cells.

20. The method of any one of claims 1–3, wherein said nucleic acid molecules, when introduced into the mammalian cells, inhibit a function of a gene in the mammalian cells.

21. The method of claim 1, wherein the gelatin is selected from the group consisting of a protein gelatin, a hydrogel, a sugar-based gelatin or a synthetic gelatin.

22. The method of claim 21, wherein the gelatin is present at a concentration in the nucleic acid molecule-containing mixture ranging from about 0.05% to about 0.5%.

23. The method of claim 22, wherein the concentration of gelatin is from about 0.1% to about 0.2%.

24. The method of claim 2, wherein the gelatin is selected from the group consisting of a protein gelatin, a hydrogel, a sugar-based gelatin or a synthetic gelatin.

25. The method of claim 24, wherein the gelatin is present at a concentration in the nucleic acid molecule-containing mixture ranging from about 0.05% to about 0.5%.

26. The method of claim 25, wherein the concentration of gelatin is from about 0.1% to about 0.2%.

27. The method of claim 3, wherein the gelatin is selected from the group consisting of a protein gelatin, a hydrogel, a sugar-based gelatin or a synthetic gelatin.

28. The method of claim 22, wherein the gelatin is present at a concentration in the nucleic acid molecule-containing mixture ranging from about 0.01% to 0.05%.

29. The method of claim 23, wherein said sugar is sucrose ranging in concentration from about 0.1M to about 0.4M.

30. The method of any one of claims 21, 24, or 27, wherein the gelatin is Type B gelatin.

31. The method of any one of claims 21, 24, or 27, wherein each nucleic acid molecule to be introduced is contained in a vector, and the surface is a slide.

32. The method of claim 31, wherein the vector is an expression vector and said nucleic acid molecules are expressed in the mammalian cells.

33. The method of any one of claims 1–3, wherein at least two different nucleic acid molecules are co-transfected into a mammalian cell.

34. The method of any one of claims 1–3, wherein said affixed plurality of nucleic acid molecules form an array of nucleic acid molecules and wherein said cells into which the nucleic acid molecules are introduced form an array of cells comprising the nucleic acid molecules.

35. The method of claim 34, wherein the gelatin is selected from the group consisting of a protein gelatin, a hydrogel, a sugar-based gelatin or a synthetic gelatin.

36. The method of claim 34, wherein the array comprises at least 96 different discrete, defined locations of known sequence composition.

37. The method of claim 36, wherein the array comprises at least 192 different discrete, defined locations of known sequence composition.

38. The method of claim 37, wherein the array comprises up to 10,000 to 15,000 different discrete, defined locations of known sequence composition.

39. The method of claim 34, wherein each of the defined locations is 100–200 µm in diameter.

40. The method of claim 39, wherein each of the defined locations is 200–500 µm apart from each other.

41. A method of introducing DNA molecules into eukaryotic cells comprising:
(a) depositing a plurality of DNA molecule-containing mixtures onto a surface in discrete, defined locations, wherein each of the DNA molecule-containing mixtures comprises a DNA molecule to be introduced into eukaryotic cells and a gelatin, wherein the concentration of DNA in said DNA molecule-containing mixtures is 0.01 µg/µL to 0.5 µg/µL;
(b) allowing the DNA molecule-containing mixtures to dry on the surface, thereby producing a surface having the DNA molecule-containing mixtures affixed thereon in discrete, defined locations; and
(c) plating the eukaryotic cells onto the surface in sufficient density and under appropriate conditions for entry of the DNA molecules in the DNA molecule-containing mixtures into eukaryotic cells; whereby the DNA molecules are introduced into the eukaryotic cells in the location in which each of the nucleic acid molecule-containing mixtures was deposited.

42. The method of claim 41, further comprising the steps after step (b) of:
(i) covering the surface bearing the DNA molecule-containing mixtures with an appropriate amount of a lipid-based transfection reagent and maintaining the resulting product under conditions appropriate for complex formation between the DNA molecules in the DNA molecule-containing mixture and the transfection reagent; and
(ii) removing the non-complexed transfection reagent.

43. The method of claim 41, wherein said DNA molecule-containing mixtures further comprise a sugar, a buffer that facilitates DNA molecule condensation, and an appropriate lipid-based transfection reagent.

44. The method of any one of claims 41–43, wherein each DNA molecule to be introduced is contained in a vector.

45. The method of claim 44, wherein the vector is an episomal vector or a chromosomally integrated vector.

46. The method of claim 44, wherein the vector is a plasmid or a viral-based vector.

47. The method of claim 46, wherein the vector is an expression vector.

48. The method of claim 47, wherein said DNA molecules are expressed in the eukaryotic cells.

49. The method of any one of claims 41–43, wherein the surface is glass, polystyrene or plastic, optionally coated with poly-L-lysine.

50. The method of any one of claims 41–43, wherein the surface is the surface of a slide.

51. The method of claim 50, wherein the slide is a glass slide coated with poly-L-lysine or a gamma-amino propyl silane slide.

52. The method of any one of claims 41–43, wherein the eukaryotic cells are mammalian cells.

53. The method of any one of claims 41–43, wherein said DNA molecules encode polypeptides that are expressed in the eukaryotic cells.

54. The method of any one of claims 41–43, wherein said DNA molecules, when introduced into the eukaryotic cells, inhibit a function of a gene in the eukaryotic cell.

55. The method of claim 41, wherein the gelatin is selected from the group consisting of a protein gelatin, a hydrogel, a sugar-based gelatin or a synthetic gelatin.

56. The method of claim 55, wherein the gelatin is present at a concentration in the DNA molecule-containing mixture ranging from about 0.05% to about 0.5%.

57. The method of claim 56, wherein the concentration of gelatin is from about 0.1% to about 0.2%.

58. The method of claim 42, wherein the gelatin is selected from the group consisting of a protein gelatin, a hydrogel, a sugar-based gelatin or a synthetic gelatin.

59. The method of claim 58, wherein the gelatin is present at a concentration in the DNA molecule-containing mixture ranging from about 0.05% to about 0.5%.

60. The method of claim 58, wherein the concentration of gelatin is from about 0.1% to about 0.2%.

61. The method of claim 43, wherein the gelatin is selected from the group consisting of a protein gelatin, a hydrogel, a sugar-based gelatin or a synthetic gelatin.

62. The method of claim 61, wherein the gelatin is present at a concentration in the DNA molecule-containing mixture is from about 0.01% to 0.05%.

63. The method of claim 62, wherein said sugar is sucrose ranging in concentration from about 0.1M to about 0.4M.

64. The method of any one of claims 55, 56, or 61, wherein the gelatin is Type B gelatin.

65. The method of any one of claims 55, 56 or 61, wherein the eukaryotic cells are plated at high density onto the surface, each DNA molecule to be introduced is contained in a vector, and the surface is a slide.

66. The method of claim 65, wherein the vector is an expression vector and said DNA molecules are expressed in the eukaryotic cells.

67. The method of any one of claims 41–43, wherein at least two different DNA molecules are co-transfected into a eukaryotic cell.

68. The method of any one of claims 41–43, wherein said affixed plurality of DNA molecules form an array of DNA molecules and wherein said cells into which the DNA molecules are introduced form an array of cells comprising the DNA molecules.

69. The method of claim 68, wherein the gelatin is selected from the group consisting of a protein gelatin, a hydrogel, a sugar-based gelatin or a synthetic gelatin.

70. The method of claim 68, wherein the array comprises at least 96 different discrete, defined locations of known sequence composition.

71. The method of claim 70, wherein the array comprises at least 192 different discrete, defined locations of known sequence composition.

72. The method of claim 71, wherein the array comprises up to 10,000 to 15,000 different discrete, defined locations of known sequence composition.

73. The method of claim 68, wherein each of the defined locations is 100–200 $\mu$m in diameter.

74. The method of claim 73, wherein each of the defined locations is 200–500 $\mu$m apart from each other.

75. The method of claim 68, wherein said DNA molecules encode polypeptides that are expressed in the eukaryotic cells.

76. The method of claim 68, wherein said DNA molecules, when introduced into the eukaryotic cells, inhibit a function of a gene in the eukaryotic cells.

77. A method of introducing nucleic acid molecules into eukaryotic cells comprising:
   (a) depositing a plurality of nucleic acid molecule-containing mixtures onto a surface in discrete, defined locations, wherein each of the nucleic acid molecule-containing mixtures comprises a nucleic acid molecule to be introduced into eukaryotic cells and a gelatin, wherein the gelatin is selected from the group consisting of a protein gelatin, a hydrogel, a sugar-based gelatin or a synthetic gelatin, and is present at a concentration from about 0.05% to about 0.5%;
   (b) allowing the nucleic acid molecule-containing mixtures to dry on the surface, thereby producing a surface having the nucleic acid molecule-containing mixtures affixed thereon in discrete, defined locations; and
   (c) plating the eukaryotic cells onto the surface in sufficient density and under appropriate conditions for entry of the nucleic acid molecules in the nucleic acid molecule-containing mixtures into eukaryotic cells; whereby the nucleic acid molecules are introduced into the eukaryotic cells in the location in which each of the nucleic acid molecule-containing mixtures was deposited.

78. The method of claim 77, further comprising the steps after step (b) of:
   (i) covering the surface bearing the nucleic acid molecule-containing mixtures with an appropriate amount of a lipid-based transfection reagent and maintaining the resulting product under conditions appropriate for complex formation between the nucleic acid molecules in the nucleic acid molecule-containing mixture and the transfection reagent; and
   (ii) removing the non-complexed transfection reagent.

79. The method of claim 77, wherein said nucleic acid molecule-containing mixtures further comprise a sugar, a buffer that facilitates nucleic acid molecule condensation, and an appropriate lipid-based transfection reagent.

80. The method of any one of claims 77–79, wherein each nucleic acid molecule to be introduced is contained in a vector.

81. The method of claim 80, wherein the vector is an episomal vector or a chromosomally integrated vector.

82. The method of claim 80, wherein the vector is a plasmid or a viral-based vector.

83. The method of claim 82, wherein the vector is an expression vector.

84. The method of claim 83, wherein said nucleic acid molecules are expressed in the eukaryotic cells.

85. The method of any one of claims 78–79, wherein the surface is glass, polystyrene or plastic, optionally coated with poly-L-lysine.

86. The method of any one of claims 77–78, wherein the surface is the surface of a slide.

87. The method of claim 86, wherein the slide is a glass slide coated with poly-L-lysine or a gamma-amino propyl silane slide.

88. The method of any one of claims 77–79, wherein the eukaryotic cells are mammalian cells.

89. The method of any one of claims 77–79, wherein said nucleic acid molecule is an oligonucleotide, DNA, or RNA.

90. The method of claim 89, wherein said nucleic acid molecule is DNA.

91. The method of any one of claims 77–79, wherein said nucleic acid molecules encode polypeptides that are expressed in the eukaryotic cells.

92. The method of any one of claims 77–79, wherein said nucleic acid molecules, when introduced into the eukaryotic cells, inhibit a function of a gene in the eukaryotic cell.

93. The method of claim 77, wherein the concentration of gelatin is from about 0.1% to about 0.2%.

94. The method of claim 78, wherein the gelatin is selected from the group consisting of a protein gelatin, a hydrogel, a sugar-based gelatin or a synthetic gelatin.

95. The method of claim 94, wherein the concentration of gelatin is from about 0.1% to about 0.2%.

96. The method of claim 79, wherein the gelatin is selected from the group consisting of a protein gelatin, a hydrogel, a sugar-based gelatin or a synthetic gelatin.

97. The method of claim 96, wherein said sugar is sucrose ranging in concentration from about 0.1M to about 0.4M.

98. The method of any one of claims 77, 94, or 96, wherein the gelatin is Type B gelatin.

99. The method of any one of claims 77, 94, or 96, wherein the eukaryotic cells are plated at high density onto the surface, each nucleic acid molecule to be introduced is contained in a vector, and the surface is a slide.

100. The method of claim 99, wherein the vector is an expression vector and said nucleic acid molecules are expressed in the eukaryotic cells.

101. The method of any one of claims 77–79, wherein at least two different nucleic acid molecules are co-transfected into a eukaryotic cell.

102. The method of any one of claims 77–79, wherein said affixed plurality of nucleic acid molecules form an array of nucleic acid molecules and wherein said cells into which the nucleic acid molecules are introduced form an array of cells comprising the nucleic acid molecules.

103. The method of claim 102, wherein the gelatin is selected from the group consisting of a protein gelatin, a hydrogel, a sugar-based gelatin or a synthetic gelatin.

104. The method of claim 102, wherein the array comprises at least 96 different discrete, defined locations of known sequence composition.

105. The method of claim 104, wherein the array comprises at least 192 different discrete, defined locations of known sequence composition.

106. The method of claim 105, wherein the array comprises up to 10,000 to 15,000 different discrete, defined locations of known sequence composition.

107. The method of claim 103, wherein each of the defined locations is 100–200 µm in diameter.

108. The method of claim 107, wherein each of the defined locations is 200–500 µm apart from each other.

109. The method of claim 107, wherein said nucleic acid molecules are DNA or RNA.

110. The method of claim 107, wherein said nucleic acid molecules encode polypeptides that are expressed in the eukaryotic cells.

111. The method of claim 107, wherein said nucleic acid molecules, when introduced into the eukaryotic cells, inhibit a function of a gene in the eukaryotic cell.

112. A method of introducing nucleic acid molecules into eukaryotic cells comprising:
   (a) depositing a plurality of nucleic acid molecule-containing mixtures onto a surface in discrete, defined locations, wherein each of the nucleic acid molecule-containing mixtures comprises:
      (i) a nucleic acid molecule to be introduced into eukaryotic cells,
      (ii) a gelatin, wherein the gelatin is selected from the group consisting of a protein gelatin, a hydrogel, a sugar-based gelatin or a synthetic gelatin, and is present at a concentration from about 0.01% to about 0.05%,
      (iii) a sugar,
      (iv) a buffer that facilitates nucleic acid molecule condensation, and
      (v) a lipid-based transfection reagent;
   (b) allowing the nucleic acid molecule-containing mixtures to dry on the surface, thereby producing a surface having the nucleic acid molecule-containing mixtures affixed thereon in discrete, defined locations; and
   (c) plating the eukaryotic cells onto the surface in sufficient density and under appropriate conditions for entry of the nucleic acid molecules in the nucleic acid molecule-containing mixtures into eukaryotic cells; whereby the nucleic acid molecules are introduced into the eukaryotic cells in the location in which each of the nucleic acid molecule-containing mixtures was deposited.

113. The method of claim 112, further comprising the steps after step (b) of:
   (i) covering the surface bearing the nucleic acid molecule-containing mixtures with an appropriate amount of a lipid-based transfection reagent and maintaining the resulting product under conditions appropriate for complex formation between the nucleic acid molecules in the nucleic acid molecule-containing mixture and the transfection reagent; and
   (ii) removing the non-complexed transfection reagent.

114. The method of claim 112 or 228, wherein each nucleic acid molecule to be introduced is contained in a vector.

115. The method of claim 114, wherein the vector is an episomal vector or a chromosomally integrated vector.

116. The method of claim 114, wherein the vector is a plasmid or a viral-based vector.

117. The method of claim 116, wherein the vector is an expression vector.

118. The method of claim 117, wherein said nucleic acid molecules are expressed in the eukaryotic cells.

119. The method of claim 112 or 113, wherein the surface is glass, polystyrene or plastic, optionally coated with poly-L-lysine.

120. The method of claim 112 or 113, wherein the surface is the surface of a slide.

121. The method of claim 120, wherein the slide is a glass slide coated with poly-L-lysine or a gamma-amino propyl silane slide.

122. The method of claim 112 or 113, wherein the eukaryotic cells are mammalian cells.

123. The method of claim 122, wherein the cells are plated at a density of $0.3 \times 10^5/cm^2$ to $3.0 \times 10^5/cm^2$.

124. The method of claim 123, wherein the cells are plated at a density of $0.5 \times 10^5/cm^2$ to $2.0 \times 10^5/cm^2$.

125. The method of claim 124, wherein the cells are plated at a density of $0.5 \times 10^5/cm^2$ to $1.0 \times 10^5/cm^2$.

126. The method of claim 112 or 113, wherein said nucleic acid molecule is an oligonucleotide, DNA, or RNA.

127. The method of claim 126, wherein said nucleic acid molecule is DNA.

128. The method of claim 112 or 113, wherein said nucleic acid molecule is DNA and wherein the concentration of said DNA is 0.01 µg/µl to 0.5 µg/µl.

129. The method of claim 128, wherein the concentration of said DNA is 0.02 µg/µl to 0.1 µg/µl.

130. The method of claim 112 or 113, wherein said nucleic acid molecules encode polypeptides that are expressed in the eukaryotic cells.

131. The method of claim 112 or 113, wherein said nucleic acid molecules, when introduced into the eukaryotic cells, inhibit a function of a gene in the eukaryotic cell.

132. The method of claim 113, wherein the gelatin is selected from the group consisting of a protein gelatin, a hydrogel, a sugar-based gelatin or a synthetic gelatin.

133. The method of claim 112 or 113, wherein the gelatin is Type B gelatin.

134. The method of claim 132, wherein the eukaryotic cells are plated at high density onto the surface, each nucleic acid molecule to be introduced is contained in a vector, and the surface is a slide.

135. The method of claim 134, wherein the vector is an expression vector and said nucleic acid molecules are expressed in the eukaryotic cells.

136. The method of claim 112 or 113, wherein said sugar is sucrose ranging in concentration from about 0.1M to about 0.4M.

137. The method of claim 112 or 113, wherein at least two different nucleic acid molecules are co-transfected into a eukaryotic cell.

138. The method of claim 112 or 113, wherein said affixed plurality of nucleic acid molecules form an array of nucleic acid molecules and wherein said cells into which the nucleic acid molecules are introduced form an array of cells comprising the nucleic acid molecules.

139. The method of claim 138, wherein the gelatin is selected from the group consisting of a protein gelatin, a hydrogel, a sugar-based gelatin or a synthetic gelatin.

140. The method of claim 138, wherein the array comprises at least 96 different discrete, defined locations of known sequence composition.

141. The method of claim 140, wherein the array comprises at least 192 different discrete, defined locations of known sequence composition.

142. The method of claim 141, wherein the array comprises up to 10,000 to 15,000 different discrete, defined locations of known sequence composition.

143. The method of claim 142, wherein each of the defined locations is 100–200 µm in diameter.

144. The method of claim 143, wherein each of the defined locations is 200–500 µm apart from each other.

145. The method of claim 138, wherein said nucleic acid molecules are DNA or RNA.

146. The method of claim 138, wherein said nucleic acid molecules encode polypeptides that are expressed in the eukaryotic cells.

147. The method of claim 138, wherein said nucleic acid molecules, when introduced into the eukaryotic cells, inhibit a function of a gene in the eukaryotic cell.

148. An array produced by the method of claim 34.
149. An array produced by the method of claim 68.
150. An array produced by the method of claim 102.
151. An array produced by the method of claim 138.

* * * * *